United States Patent [19]

Hirschberg

[11] Patent Number: 4,835,853
[45] Date of Patent: Jun. 6, 1989

[54] METHOD FOR ELECTRICALLY CONNECTING CONDUCTORS & ELECTRODES IN AN IMPLANTABLE ELECTRODE LEAD

[75] Inventor: Jakub Hirschberg, Taeby, Sweden

[73] Assignee: Siemens Aktiengesellschaft, Berlin and Munich, Fed. Rep. of Germany

[21] Appl. No.: 199,252

[22] Filed: May 26, 1988

[30] Foreign Application Priority Data

May 27, 1987 [EP] European Pat. Off. ........ 87107760.8

[51] Int. Cl.$^4$ ............................................ H01R 43/00
[52] U.S. Cl. ........................................ 29/854; 219/58
[58] Field of Search ............ 29/854; 128/419 P, 642, 128/784, 785, 786; 174/108, 130, 131 A, 131 B; 219/58, 97, 100

[56] References Cited

U.S. PATENT DOCUMENTS

| | | | |
|---|---|---|---|
| 3,136,032 | 6/1964 | Berndsen | 29/854 X |
| 3,701,877 | 10/1972 | Richardson | 219/97 |
| 3,769,984 | 11/1973 | Muench | 128/404 |
| 3,934,337 | 1/1976 | Palazzetti et al. | 29/628 |
| 4,253,233 | 3/1981 | Lourekorie et al. | 29/857 |
| 4,381,014 | 4/1983 | Sandstrom et al. | 128/786 |
| 4,484,586 | 11/1984 | Bumrkle et al. | 128/786 |
| 4,619,488 | 10/1986 | Martin | 29/854 X |

*Primary Examiner*—Timothy V. Eley
*Attorney, Agent, or Firm*—Hill, Van Santen, Steadman & Simpson

[57] ABSTRACT

A conductor embedded in the insulating layers of an implantable lead is connected to an electrode by arranging the conductor to be included as one pole in a high voltage circuit having another pole in the form of a needle or the like placed in the vicinity of the conductor. The voltage is increased until an insulating layer-puncturing flash-over between the conductor and the needle takes place. The flash-over arc is maintained to burn a hole in the insulation layers so that the conductor is exposed. The conductor can then be removed out with a curved tool to form a connecting end to be applied to the electrode, or a supplementary conductor can be attached to the exposed conductor for attachment to the electrode.

5 Claims, 2 Drawing Sheets

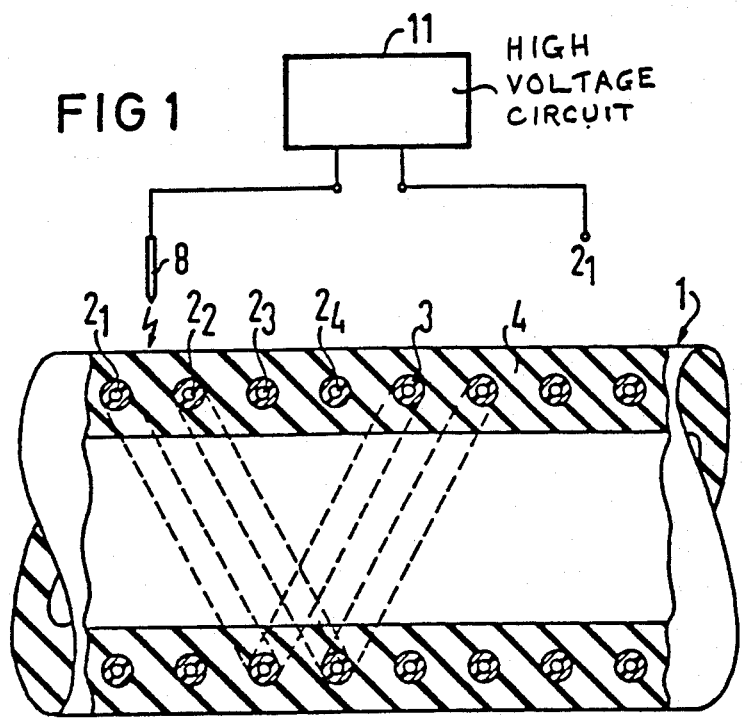
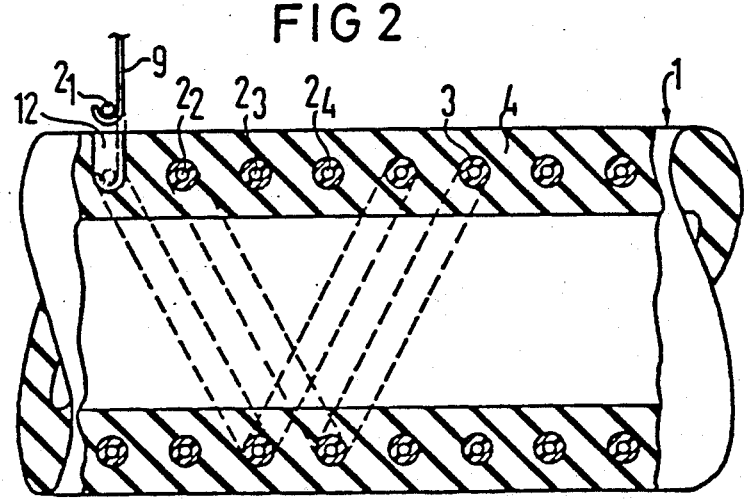

METHOD FOR ELECTRICALLY CONNECTING CONDUCTORS & ELECTRODES IN AN IMPLANTABLE ELECTRODE LEAD

BACKGROUND OF THE INVENTION

1. Field of the Invention

This invention relates to a method for electrically connecting conductors and electrodes in an implantable lead.

2. Description of the Prior Art

A lead for biomedical stimulation generally includes a lead body and one or more exposed electrodes for making electrical contact with body tissues. The lead body essentially includes one or more conductors electrically connected to the electrodes, and one or more insulating materials enclosing the conductors and also forming a lead casing. Generally, the casing is made of a flexible, body compatible material such as silicon rubber or the like. Between each electrode and the lead body there is a juncture, which is critical to the proper functioning of the lead. The juncture must withstand body fluid penetration and ensure the electrical connection between the electrode and the related conductor.

There are various known methods of making such electrical connections.

U.S. Pat. No. 4,381,014 teaches simultaneous connecting and sealing of a juncture by welding an axially extending supplementary wire to several turns of a single-pole, helix-formed conductor at predetermined electrode locations before the conductor is encased in the insulating sheath. Subsequently, the electrode is swaged to cause the wire to penetrate the insulating sheath and establish electrical connection of the conductor and the electrode. Simultaneously, the crimped (swaged) electrode seals the juncture at the ends of the electrode.

An example of a connection in a bi-polar lead is given to U.S. Pat. No. 3,769,984. The lead disclosed therein has two parallel, longitudinally extending non-helical wire conductors in an extruded lead body. The conductors are connected to a pair of axially separated electrodes at the lead distal end. The axial separation between the electrodes corresponds to the axial separation between the distal ends of the conductors, which ends are brought out from the lead body through bores and then connected to the electrodes by, for example, being clamped between a crimp ring and the electrode.

In these examples, with one or two conductors in the lead body, conductor selection at a desired electrode location does not pose a problem with respect to the connection method. In contrast, modern tubing leads, as disclosed, for example, in U.S. Pat. No. 4,484,586, require the electrodes to be attached to a tubing lead body structure comprising several, individually insulated, helically wound conductors. The axial separation between the turns of different conductors in the helix is very small, for example, about 0.2 mm. From this bundle, the conductor to be connected to a certain electrode should be quickly and reliably selected, made free from insulation and adapted for connection at a desired electrode location.

SUMMARY OF THE INVENTION

It is an object of the present invention to provide an electrode-conductor connecting method which is suitable for, but not exclusively applicable to, a conductor in a lead of the tubing type described above.

The above object is achieved in accordance with the principles of the present invention in a method wherein one of the conductors is arranged to form one pole of a high voltage circuit, the other pole of which is a puncturing element, such as a needle or the like. The needle is placed at a selected position at which it is desired to attach an electrode, and the insulating sheath in punctured by initiating an electric arc between the two poles of the high voltage circuit. By maintaining the arc, the insulation is burned at the puncturing location to form a hole by means of which the conductor which formed the pole in the high voltage circuit is exposed. A connecting end can then be formed on the exposed conductor for attachment of an electrode, either by removing the exposed conductor from the lead by a curved tool inserted through the hole, or by attaching a supplemental conductor to the exposed conductor, to which the electrode is then attached.

DESCRIPTION OF THE DRAWINGS

FIG. 1 is an axial sectional view of the lead illustrating the puncturing and the high voltage burning steps of the method disclosed herein.

FIG. 2 is an axial sectional view of the lead illustrating the step in the method disclosed herein where the conductor selected for connection is taken out with a curved tool.

DESCRIPTION OF THE PREFERRED EMBODIMENTS

Figure 3:
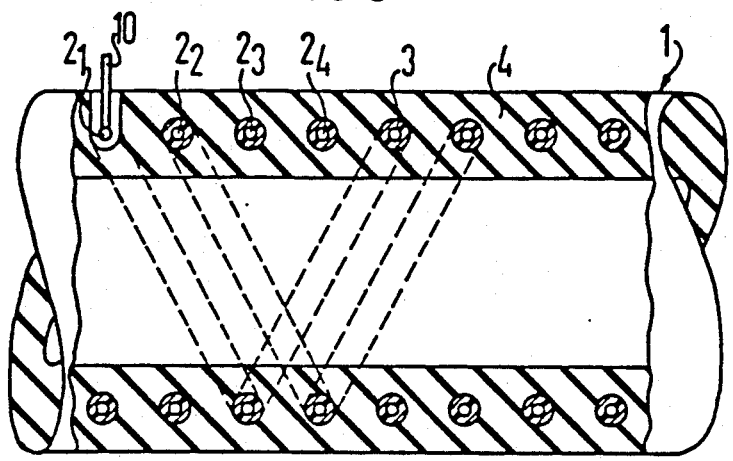
FIG. 3 is identical to FIG. 2 except that it illustrates the selected conductor being resistance welded to a supplementary electrode connecting conductor.

As shown in FIG. 1, an embodiment of the invention includes a multi-pole lead 1 having helically wound conductors in a four-pole arrangement $2_1$, $2_2$, $2_3$, $2_4$. The conductors may consist of multi-filament (e.g. refined steel) wire, which exhibits a high fatigue strength under repeated bending stress. Preferably, but not necessarily, the conductors could be surrounded by a first insulating material 3 with good electric insulating properties, viz. teflonpolymers such as FEP (Fluorinated ethylene propylene) or PTFE (Polytetrafluorethylene). The conductors are embedded in a second insulating material 4 with good body compatibility properties, e.g., silicon rubber. The conductors 2 may be individually identified by differently colored insulation, possible combined with an x-ray contrast medium.

The connecting method includes the following steps. The conductor to be connected, for example $2_1$, is arranged as one pole in a high voltage circuit 11. A puncturing means, a needle 8 or the like, is arranged as the other pole in the circuit and placed at the desired electrode location, but at a distance from the lead body.

By increasing the voltage, an electric arc is initiated between the conductor $2_1$ and the needle 8, and the insulation materials are punctured. Because the flashover takes place only between the poles in the high voltage circuit, the conductors $2_2$, $2_3$ and $2_4$ and their insulations are left undisturbed even if the conductors form a compact multi-pole helix, and the method does not require the needle 8 to be exactly located over the conductor $2_1$. By maintaining the arc, a hole (referenced 12 in FIG. 2) is burned in the insulating materials through which the conductor is made available (exposed) for the next step in the method.

In FIG. 2 the step is illustrated in which the conductor is brought out from the hole 12 with a curved tool 9. The lower position shows the inserted tool in dashed lines and the upper position shows the tool and the removed conductor. Alternatively as shown in FIG. 3, a supplementary electrode-connecting conductor 10 could be inserted into the hole 12 and connected by resistance welding to the exposed turn of the helix-formed conductor, whereby several axially separated connections to the same or different electrodes are possible, because the helix-formed conductor is not mechanically destroyed. In either case, a connecting end to be applied to the electrode is formed.

Figure 4:
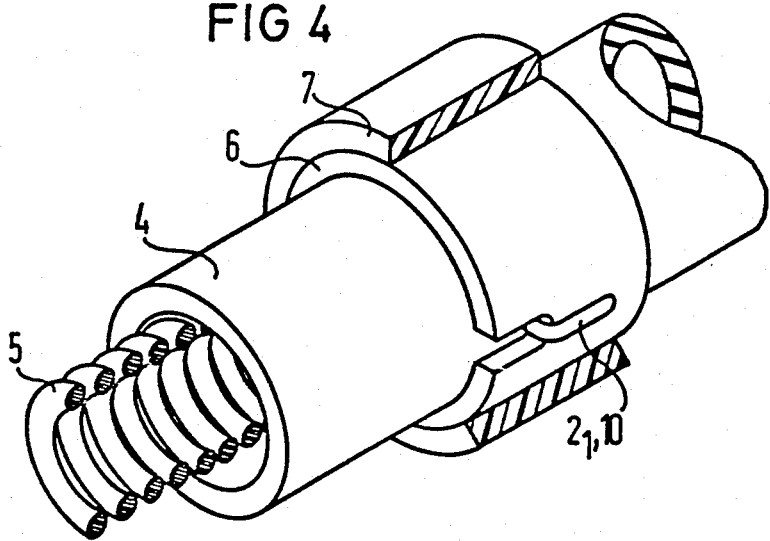
FIG. 4 is a perspective view of the lead illustrating how slitted (tubing) rings and crimp rings are applied to the lead, and the assembly of a guide coil.

Subsequently as shown in FIG. 4, in a conventional fashion, slitted (tubing) rings 6 are applied to the lead at the hole location and the connecting end is clamped between the slitted ring 6 and an electrode crimp ring 7. The slitted rings 6 and the crimp rings 7 should be of a material with good body compatibility properties such as platinum or the like. Alternately, welding could replace clamping.

Finally, and also conventionally, the lead is assembled with respect to a guide coil 5. Connector details, an electrode tip and other metal details, and rubber details (e.g. seals) are molded or glued to the lead in this assembly. The guide coil 5 conductors may be comprised of MP 35 N, possibly in a multi-filament arrangement.

Although modifications and changes may be suggested by those skilled in the art it is the intention of the inventor to embody within the patent warranted hereon all changes and modifications as reasonably and properly come within the scope of his contribution to the art.

I claim as my invention:

1. A method for preparing an implantable lead for connection to an electrode, said lead having at least one conductor to be connected to said electrode and at least one insulating sheath, said method comprising the steps of:

arranging said at least one conductor to form one pole in a high voltage circuit in which a puncturing element forms the other pole;

puncturing, at a selected electrode position, said at least one insulating sheath by initiating an electric arc between said poles of said high voltage circuit;

burning, by maintaining said arc, the insulation where punctured to form a hole through which the conductor is exposed; and forming a connecting end of the exposed conductor for attachment to said electrode.

2. A method as claimed in claim 1, wherein the step of forming a connecting end is further defined by removing the exposed conductor from said lead by a tool inserted through said hole.

3. A method as claimed in claim 1, herein the step of forming a connecting end is further defined by connecting a supplementary conductor to said exposed conductor by resistance welding.

4. A method for preparing an implantable lead for connection to an electrode, said lead having at least one conductor to be connected to said electrode and at least one insulating sheath, said method comprising the steps of:

arranging said at least one conductor to form one pole in a high voltage circuit in which a puncturing element forms the other pole;

puncturing, at a selected electrode position, said at least one insulating sheath by initiating an electric arc between said poles of said high voltage circuit;

burning, by maintaining said arc, the insulation where punctured to form a hold through which the conductor is exposed; and removing said exposed conductor through said hole with a tool for attachment to said electrode.

5. A method for preparing an implantable lead for connection to an electrode, said lead having at least one conductor to be connected to said electrode and at least one insulating sheath, said method comprising the steps of:

arranging said at least one conductor to form one pole in a high voltage circuit in which a puncturing element forms the other pole;

puncturing, at a selected electrode position, said at least one insulating sheath by initiating an electric arc between said poles of said high voltage circuit;

burning, by maintaining said arc, the insulation where punctured to form a hole through which the conductor is exposed; and attaching a supplementary conductor through said hole to said exposed conductor by resistance welding for attachment to said electrode.

* * * * *